United States Patent [19]

Young

[11] Patent Number: 5,288,692
[45] Date of Patent: Feb. 22, 1994

[54] SYSTEMIC HERBICIDES AND METHODS OF USE

[75] Inventor: Donald C. Young, Fullerton, Calif.

[73] Assignee: Union Oil Company of California, Los Angeles, Calif.

[21] Appl. No.: 707,322

[22] Filed: Dec. 27, 1990

Related U.S. Application Data

[63] Continuation of Ser. No. 116,472, Nov. 3, 1987, Pat. No. 4,994,101, which is a continuation-in-part of Ser. No. 442,296, Nov. 17, 1982, abandoned, and a continuation-in-part of Ser. No. 453,496, Dec. 27, 1982, Pat. No. 4,910,179.

[51] Int. Cl.$^5$ .................................... A01N 57/12
[52] U.S. Cl. ..................... 504/127; 504/130; 504/133; 504/137; 504/143; 504/148; 504/149; 504/140
[58] Field of Search ............ 71/79, 83, 86, 98, 99, 71/118, 119; 504/127, 130, 133, 137, 143, 148, 149

[56] References Cited

U.S. PATENT DOCUMENTS

| | | | |
|---|---|---|---|
| 4,116,664 | 9/1978 | Jones | 71/549 |
| 4,214,888 | 7/1980 | Young | 71/28 |
| 4,310,343 | 1/1982 | Verdagaal et al. | 71/29 |
| 4,315,763 | 2/1982 | Stoller et al. | 71/29 |
| 4,397,675 | 11/1981 | Young | 71/28 |
| 4,402,852 | 12/1981 | Young | 71/182 |
| 4,404,116 | 12/1981 | Young | 252/182 |
| 4,445,925 | 11/1981 | Young | 71/28 |
| 4,447,253 | 11/1981 | Young | 71/28 |
| 4,512,813 | 4/1985 | Young | 134/27 |
| 4,626,417 | 12/1986 | Young | 423/235 |
| 4,818,269 | 4/1989 | Young | 71/83 |
| 4,834,788 | 5/1989 | Young | 71/83 |
| 4,879,413 | 11/1989 | Buser et al. | 564/63 |
| 4,910,179 | 3/1990 | Young | 502/167 |

OTHER PUBLICATIONS

New Weed Management Practices In Orchards, Neil H. Phillips, Proceedings, 36 Annual California Weed Conference, Jan. 16-19, 1984.

Federal Register Notice of Mar. 13, 1985, pp. 10006-10007, "Monourea-Sulfuric Acid Adduct".

CA 102:41512m, Comparative Phytotoxicity of Glyphosate, SC-0224, SC-0545, and HOE-00661, Carlson and Burnside, Weed Science, 1984, 32, 841-844.

CA 89:158688c, "Complexing Agents as Herbicide Additives," Turner and Loader, Weed Research, 1978, 18, 199-207.

(List continued on next page.)

*Primary Examiner*—Glennon H. Hollrah
*Assistant Examiner*—Brian M. Burn
*Attorney, Agent, or Firm*—Michael H. Laird; Yale S. Finkle; Gregory F. Wirzbicki

[57] ABSTRACT

Herbicidal compositions having systemic herbicidal activity comprise solutions containing one or more systemic herbicides and an amount of an amide and sulfuric acid of the following formula sufficient to accentuate the activity of the systemic herbicide:

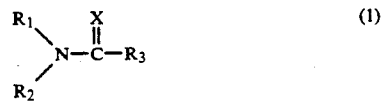

(1)

wherein X is chalcogen, and each of $R_1$, $R_2$ and $R_3$ is independently selected from hydrogen and organic radicals. As used herein, "amide" encompasses all compounds of formula (1) regardless of the chalcogen employed. The molar ratio of amide to sulfuric acid is usually within the range of about ½ to less than 2 so that at least some of the sulfuric acid is present as the monoamide-sulfuric acid adduct. The monoamide adduct also acts as a contact herbicide and thereby assists in the immediate control of treated vegetation. Solid compositions comprising combinations of systemic herbicides, sulfuric acid and the useful amides, with and without surfactants, and methods of using the solutions are also disclosed.

29 Claims, No Drawings

OTHER PUBLICATIONS

CA 98:174739m, "Effect of Water Quality, Carrier Volume and Acid on Glyphosate Phytotoxicity," Buehler and Burnside, Weed Science, 1983, 31:163–169.

Donald C. Young, U.S. patent application Ser. No. 07/116,472, filed Nov. 3, 1987 for Systemic Herbicides and Methods of Use.

D. F. du Toit, Verslag Akad. Wetenschappen, 22, 573–4 (abstracted in Chemical Abstracts, 8, 2346 (1914)).

L. H. Dalman, "Ternary Systems of Urea and Acids. I. Urea, Nitric Acid and Water. II. Urea, Sulfuric Acid and Water. III. Urea, Oxalic Acid and Water"; JACS, 56, 549–53 (1934).

Sulfur Institute Bulletin No. 10 (1964), "Adding Plant Nutrient Sulfur to Fertilizer".

Farm Chemicals Handbook, Meister Publishing Company, Willoughby, Ohio 44094 (1981), p. C316.

Adalla, "Effects of Herbicidal Weed Control on Growth and Development of Ground Nuts (*Arachis hypogaea* I.) in Western Kenya," Proceedings of the East African Weed Science Conference, 6, 1976, pub. 1977; Chemical Abstracts, 93, 93:990069b, 1980.

Bach et al., "Destroying Potato Plants", East German Patent 146,541, Feb. 18, 1981, Chemical Abstracts, 95, 95:3711g (1981), (only the abstract is cited).

Chan, Chemical Abstract vol. 98 (1978) 131776e.

Kamilova et al., Chemical Abstracts vol. 93 (1980) 63397w.

SYSTEMIC HERBICIDES AND METHODS OF USE

RELATED APPLICATIONS

This application is a continuation of my co-pending application Ser. No. 07/166,472, filed Nov. 3, 1987, now U.S. Pat. No. 4,994,101, issued Feb. 19, 1991, which was a continuation-in-part of my copending application Ser. No. 442,296, filed Nov. 17, 1982, now abandoned, for SYSTEMIC HERBICIDAL COMPOSITIONS AND METHODS OF USE and Ser. No. 453,496, filed Dec. 27, 1982, now U.S. Pat. No 4,910,179 for ACID CATALYZED REACTIONS AND COMPOSITIONS USEFUL THEREIN.

BACKGROUND

1. Field of the Invention

This invention relates to the field of herbicidal compositions, and particularly to compositions having contact herbicidal activity and accentuated systemic herbicidal activity, and to methods of using such compositions to control vegetation.

2. Description of the Art

Both urea and sulfuric acid are widely used for a variety of purposes in numerous industries as fertilizers, soil adjuvants, chemical treating agents, chemical precursors and reactants. They are sometimes useful in combination, particularly in the agricultural industry, when the simultaneous addition of urea and sulfur to the soil is desired. Sulfuric acid is known to be phytotoxic, has been used as a postemergent, contact herbicide on a variety of plants, and is registered with the United States Environmental Protection Agency for the elimination of certain weed plants from plots of growing onions and garlic.

A variety of systemic herbicides are well known and are commercially available. Some of these such as Roundup ®, the isopropylamine salt of N-(phosphonomethyl) glycine, are relatively broad spectrum in that they are active toward a wide variety of vegetation. Others are relatively more selective in that they preferentially attack a relatively limited spectrum of plant species. For instance, some systemics such as 2,4-dichlorophenoxyacetic acid, known as 2,4-D, can be used to preferentially control broadleafs in the presence of grasses. Others such as 2,2-dichloropropionic acid, known as Dalapon and by other names, selectively control grasses in the presence of broadleafs. Other types of selectivity are also available.

Systemic herbicides are those that are assimilated by susceptible vegetation and are then translocated to parts of the plant other than those contacted, The systemic herbicides generally, if not always, depend on such translocation for their activity. For instance, when applied to plant foliage, a systemic herbicide will be assimilated during transpiration, or otherwise, and transported throughout the entire plant so that it eliminates the undesired vegetation, roots and all.

Some systemic herbicides are effective only when applied to established, transpiring vegetation and are known as postemergent herbicides. Others, that may or may not be active postemergent, are also effective preemergent herbicides. Preemergent herbicides are assimilated either by the plant seed prior to germination, and/or are stable in the soil environment and enter the cotyledon—the first leaf, leaf pair, or whorl of leaves developed by the seed plant embryo—and thereafter translocate to and destroy all parts of the germinating seed prior to or shortly after emergence. A variety of pre- and postemergent systemic herbicides are identified, and their chemical and herbicidal properties are disclosed in the Farm Chemicals Handbook published annually by *Farm Chemicals Magazine*, Meister Publishing Company, Willoughby, Ohio.

A number of investigators have studied the effects of combining systemic herbicides with certain contact herbicides (other than those described herein), and consistently have found that the systemic herbicide's activity is markedly reduced or is eliminated altogether when used in such combinations. Furthermore, all of the known systemic herbicides are complex organic compounds that are chemically unstable in the presence of relatively concentrated sulfuric acid. Therefore, they cannot be used in combinations in which the contact herbicidal activity or soil adjuvant properties of sulfuric acid might be desirable.

Other problems associated with presently available systemic herbicidal compositions include their ecotoxicity, persistence in the environment, high cost of application at effective dosage rates, the lack of effective immediate vegetation control such as that available with contact herbicides, limited effectiveness on some more resistant forms of vegetation, and others. Accordingly, a need exists for improved systemic herbicidal compositions and methods of vegetation control capable of minimizing or eliminating these problems.

It is, therefore, a primary object of this invention to provide improved herbicidal compositions, solid compositions convertible to herbicidal compositions, and methods for the use of such compositions.

Another object of this invention is the provision of systemic herbicidal compositions with increased activity of the contained systemic herbicides.

Another object of this invention is the provision of herbicidal compositions and methods of their use which significantly reduce the amount of systemic herbicide required to control undesired vegetation, and thereby reduce the amount of systemic herbicide introduced into the environment.

Another object of this invention is the provision of compositions which exhibit both significant contact and systemic herbicidal activity and/or methods of their use.

Another object is the provision of compositions and methods for controlling undesired vegetation and simultaneously applying nutrient nitrogen and sulfur to the soil.

Another object is the provision of compositions containing significant amounts of sulfuric acid and one or more systemic herbicides that are chemically stable in the composition.

Other objects, aspects, and advantages of this invention will be apparent to one skilled in the art in view of the following disclosure and the appended claims.

SUMMARY OF THE INVENTION

Briefly, the invention provides improved (1) liquid herbicidal compositions, (2) solid compositions which dissolve in water to form such liquid herbicidal compositions, and (3) methods for the use of such herbicidal compositions.

The novel liquid herbicidal compositions are solutions of one or more pre- and/or postemergent systemic herbicides and a mixture of sulfuric acid and an amide of the formula

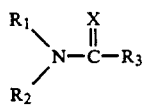

wherein X is a chalcogen, each of $R_1$, $R_2$, and $R_3$ is independently selected from hydrogen and monovalent organic radicals, and $R_1$ and $R_2$, together, can be a divalent organic radical, in which the molar ratio of amide to sulfuric acid is within the range of about $\frac{1}{4}$ to less than 2 so that at least some of the sulfuric acid is present as the monoamide-sulfuric acid adduct. The systemic herbicides (defined in more detail hereinafter) are sufficiently stable in the presence of the amide-sulfuric acid compositions to allow their use in the compositions and methods of this invention.

The novel solid compositions are solid mixtures of one or more pre- and/or postemergent, systemic herbicides and a combination of sulfuric acid and the useful amides in which the molar ratio of amide to sulfuric acid is within the range of about $\frac{1}{4}$ to less than 2 so that at least some of the sulfuric acid is present as the monoamide-sulfuric acid adduct.

The liquid and solid compositions may also contain one or more surfactants chemically stable in the presence of the combination of amide and sulfuric acid. Surfactants improve both the foliage coverage by and the herbicidal activity of the aqueous solutions.

The methods of the invention involve the application of the aforedescribed liquid or solid herbicidal compositions to vegetation and/or to the soil (when preemergent activity is desired) at dosage rates sufficient to control undesired vegetation, seeds and/or unemerged seedlings.

The compositions and methods of this invention have surprisingly accentuated pre- and postemergent, systemic herbicidal activity with the result that significantly smaller dosages of a given herbicide may be applied to achieve the same degree of vegetation control or, alternatively, a higher degree of vegetation control is achieved with the same application rate. These compositions and methods also provide contact herbicidal properties and, at the same time, provide nitrogen and sulfur nutrients for the desired plants. They also enable the use of systemic herbicides in combination with relatively concentrated sulfuric acid.

The available contact herbicidal activity provides immediate vegetation control while the improved systemic herbicidal activity reduces treatment cost, improves vegetation control, reduces both immediate and residual toxic effects to humans, and reduces the possibility of herbicide residue on harvested food crops.

DETAILED DESCRIPTION OF THE INVENTION

This invention provides novel compositions with systemic herbicidal properties and methods for use of such compositions to control vegetation. The compositions can be either solid or liquid and they contain one or more systemic herbicides, a combination of sulfuric acid and an amide of the formula

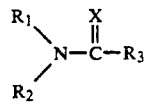

wherein X is a chalcogen, each of $R_1$, $R_2$ and $R_3$ is independently selected from hydrogen and monovalent radicals, and $R_1$ and $R_2$, together, can form a divalent organic radical. The molar ratio of amide to sulfuric acid is within the range of about $\frac{1}{4}$ to less than 2 so that at least some of the sulfuric acid is present as the monoamide-sulfuric acid adduct, and the composition may optionally contain a surfactant. As used herein, "amide" includes all components of formula (1) regardless of the chalcogen employed.

When $R_1$, $R_2$ and $R_3$ are organic radicals, they may be cyclic or acyclic, straight or branched chained and can contain one or more hetero atoms such as sulfur, nitrogen, oxygen, phosphorus and the like. Further, they can contain one or more substituents such as thiol, hydroxy, nitro, amino, nitrile, amide, ester and halogen groups and others. Such organic radicals may contain aryl groups, such as aralkyl and alkaryl groups. The preferred organic radicals are free of olefinic or alkynyl unsaturation and generally have up to about 20, preferably up to about 10 carbon atoms. Particularly preferred amides are urea, thiourea, formamide, dimethylformamide, biuret, triuret, thioformamide, and combinations of these.

The chalcogens are elements of Periodic Group VI-B and include oxygen, sulfur, selenium, tellurium, and polonium. Oxygen and sulfur are presently preferred due to low cost, availability, low toxicity and chemical activity, and oxygen is the most preferred.

The compositions can be used for immediate and long-term, pre- and postemergent control of essentially any form of vegetation, particularly upon appropriate selection of the systemic herbicidal component or components. Immediate vegetation control by contact killing of more resistant plants may require higher concentrations and/or higher dosage rates of the monoamide adduct. Longer term control can be achieved through the selection of a systemic component that is particularly active for the controlled plant species. Thus, these compositions can be used for both immediate and long-term control of all varieties of vegetation including those usually found in agricultural fields such as bushes, scrub brush, vines, and other weeds.

Illustrative of vegetation that can be controlled by these methods, with or without the use of surfactants are: black mustard (*brassica nigra*), curly dock (*rumex crispus*), common groundsel (*senecio vulgaris*), pineapple weed (*matricaria matricarioides*), swamp smartweed (kelp) (*polygonum coccineum*), prickly lettus (*lactuca scariola*), lance-leaved groundcherry (*physalis lanceifolia*), annual sowthistle (*sonchus oleraceus*), london rocket (*sisymbrium irio*), common fiddleneck (*amsinckia intermedia*), hairy nightshade (*solanum sarrachoides*), shepherd's purse (*capsella bursa-pastoris*), sunflower (*helianthus annus*), common knotweed (*polygonum aviculare*), green amaranth (*amaranthus hybridus*), mare's tail (*conyza canadensis*), henbit (*lamium amplexicaule*), cocklebur (*xanthium strumarium*), cheeseweed (*malva parviflora*), lambsquarters (*chenopodium album*), puncture vine (*tribulus terrestris*) common purslane (*portulaca oleracea*), prostrate spurge (*euphorbia supina*), telegraph plant (*heterotheca grandiflora*), carpetweed (*mollugo verticillata*), yellow starthistle (*centaurea solstitialis*), milk thistle (*silybum marianum*), mayweed (*anthemis cotula*), burning nettle (*urtica urens*), fathen (*atriplex patula*), chickweed (*stellaria media*), scarlet pimpernel (*anagallis arvensis*) redroot pigweed (*amaranthus retroflexus*), minnerslettuce (*montia perfoliata*), turkey mullein (*eremocarpus setigerus*), nettleleaf goosefoot (*chenopodium murale*), prostrate pigweed (*amaranthus blitoides*), silverleaf nightshade (*solanum elaeagnifolium*), hoary cress (*cardaria draba*), largeseed dodder (*cuscuta indecora*), California burclover (*medicago polymorpha*), horse purslane (*trianthema portulacastrum*), field bindweed (*Iconvolvulus arvensis*), Russian knapweed (*centaurea repens*), flax-leaved fleabane (*conyza bonariensis*), wild radish (*raphanus sativus*), tumble pigweed (*amaranthus albus*), stephanomeria (*stephanomeria exigua*), wild turnip (*brassica campestris*), buffalo goard (*cucurbita foetidissima*), common mullein (*verbascum thapsus*), dandelion (*taraxacum officinale*), Spanish thistle (*xanthium spinosum*), chicory (*cichorium intybus*), sweet anise (*foeniculum vulgare*), annual yellow sweetclover (*melilotus indica*), poison hemlock (*conium maculatum*), broadleaf filaree (*erodium botrys*), whitestem filaree (*erodium moschatum*), redstem filaree (*erodium cicutarium*), ivyleaf morning-glory (*ipomea hederacea*), shortpod mustard (*brassica geniculata*), buckhorn plantain (*plantago lacenolata*), sticky chickweed (*cerastium viscosum*), himalaya blackberry (*rubus procerus*), purslane speedwell (*veronica peregrina*), Mexican tea (*chenopodium ambrosioides*), Spanish clover (*lotus purshianus*), Australian brassbuttons (*cotula australis*), goldenrod (*solidago californica*), citron (*citrullus lanatus*), hedge mustard (*sisymbrium orientale*), black nightshade (*solanum nodiflorum*), Chinese thornapple (*datura ferox*), bristly ox tongue (*picris echioides*), bull thistle (*cirsium vulgare*), spiny sowthistle (*sonchus asper*), Tasmanian goosefoot (*chenopodium pumilio*), goosefoot (*chenopodium botrys*), wright groundcherry (*physalis acutifolia*), tomatillo groundcherry (*physalis philadelphica*), pretty spurge (*euphorbia peplus*), bitter apple (*cucumis myriocarpus*), indian tobacco (*nicotiana bigelovii*), common morning-glory (*ipomoea purpurea*), waterplantain (*alisma triviale*), smartweed (*polygonum lapathifolium*), mature sowthistle (*sonchus asper*), yellow nutsedge (*cyperus esculentus*), purple nutsedge (*cyperus rotundus*), lupine (*lupinus formosus*), and grasses of the family Gramineae such as annual rye grass, blue grass, water grass, barnyard grass, bermuda grass, fescue, mat grass, Johnson grass, and the like.

The systemic herbicides are selected in view of the type of control desired (i.e. preemergent or postemergent) and the type of vegetation to be controlled according to the known attributes of the herbicides. Additionally, the systemic herbicides should be sufficiently chemically stable in both the solid and liquid compositions to assure that the herbicide retains its activity for the period of time required to manufacture, store, transport, and apply the compositions. The stability of the systemic herbicide can be readily determined by adding an amount of the herbicide to the amide-sulfuric acid composition in which it is to be employed and monitoring the combination by nuclear magnetic resonance (NMR). NMR can be used to monitor the frequency and magnitude of spectral peaks characteristic of a selected nucleus in the subject molecule; i.e. the systemic herbicide. Persistent spectral peak magnitude and frequency over a period of 5 to 6 hours indicate stability. Diminished magnitude or a shift in peak frequency associated with the selected nucleus indicates instability, i.e. that the arrangement of functional groups has been modified.

The systemic herbicide should also preferably be water-soluble, although relatively water-insoluble systemic herbicides may be used if a surfactant or mechanical agitation is employed to disperse the herbicide throughout the solution. Essentially all systemic herbicides are either water-soluble or are commercially available as dispersions or solutions in water-dispersible oils, all of which are readily dispersible or soluble in water.

Suitable systemic herbicides include all preemergent and postemergent systemic herbicides that are sufficiently chemically stable and dispersible as discussed above. As used herein, the terms "preemergent" and "postemergent" refer to the plant to be controlled and not to a desirable crop plant that has been seeded or that is growing in the treated area. The compositions and methods of this invention are particularly beneficial when using systemic herbicides having postemergent activity, i.e. systemic herbicidal activity toward established plants, due to the dramatic improvements in postemergent, systemic activity available with these compositions and methods. Exemplary herbicides include Chlorpropham, Propham, Oxyfluorfen, Endothall, Roundup ®, and the like.

Chlorpropham, also known as CHLORO IPC®, Furloe®, and by other designations, contains the active ingredient isopropyl-N-m-chlorophenylcarbamate, manufactured by PPG Industries, Inc., and others having the formula:

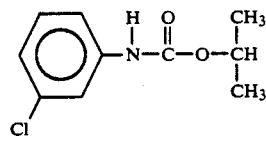

This herbicide has both preemergent and postemergent activity and is effective for the control of weeds in alfalfa, lima and snap beans, blueberries, caneberries, cranberries, carrots, ladino clover, garlic, seed grass, onions, spinach, sugar beets, and several other crops.

Propham, also known as IPC, contains the active ingredient isopropyl carbanilate having the formula:

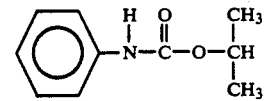

This herbicide also has both postemergent and preemergent activity and is effective for the control of weeds in alfalfa, flax, lettuce, red or crimson clover, ladino, spinach, sugar beets and several other crops.

Oxyfluorfen, sold under the tradenames Goal®, Koltar®, and others, contains the active ingredient 2-chloro-1-(3-ethoxy-4-nitrophenoxy)-4-(trifluoromethyl) benzene having the formula:

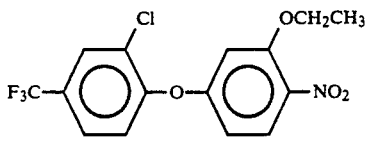

This herbicide is effective for both pre- and postemergent control of a broad spectrum of annual grasses and broadleaf weeds in crops such as soybeans, corn, cotton, tree fruits, grapes, nuts, and a variety of tropical plantation and ornamental crops.

Endothall, sold under a variety of names including Accelerate®, Aquathol®, Hydout®, and others, contains the active ingredient 7-oxabicyclo-(2,2,1)-heptane-2,3-dicarboxylic acid, usually as the sodium, potassium or amine salts, having the formula:

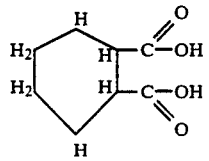

Endothall has activity as both a pre- and postemergent herbicide, defoliant, desiccant, aquatic herbicide and growth regulator, and is used as a potato vine killer, alfalfa and clover desiccant, cotton harvest aid, and on sugar beets and turf, and as an aquatic herbicide and algicide.

Glyphosate, is sold as the isopropylamine salt under the tradename Roundup®, and has the formula:

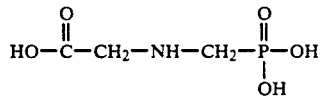

Glyphosate is a broad spectrum, postemergent, systemic herbicide effective for the control of many annual and perennial grasses and broadleaf weeds in addition to many tree and woody brush species both in cropland and noncrop sites. It is considered essentially nonselective.

The concentration of the systemic herbicide component in the liquid compositions of this invention as applied to vegetation or the soil, should be sufficient to accomplish the desired degree of pre- and/or postemergent control at the dosage rate employed. Dosage rates are discussed hereafter. Effective concentrations can be determined by reference to the manufacturer's recommendations and will usually correspond to about 10 to 50 percent, more often about 25 to 50 percent of the recommended concentration at the dosage rate recommended by the manufacturer. Manufacturer's recommended concentrations, as applied, vary widely depending on the effectiveness of the particular systemic herbicide involved, and can range from about 0.1 to about 50 weight percent, usually about 0.2 to about 10 weight percent.

Systemic herbicidal compositions usually have much higher active component concentrations as manufactured or packaged for sale and are designed for dilution prior to use. The same is true of the systemic herbicidal compositions of this invention. Thus, the concentrations of the systemic herbicidal component in the compositions of this invention are, as a practical matter, limited only by the solubility or dispersibility of the particular systemic herbicide in concentrated solutions of the amide-sulfuric acid component. The concentrated compositions, therefore, will usually contain about 0.1 to about 10 weight percent, preferably about 0.1 to about 1 weight percent of the systemic herbicide component.

The systemic herbicide component concentration employed in the solid compositions of this invention should be proportionately higher than that desired in the applied solution to assure that an adequate concentration will be present when the solid is dissolved prior to application. For example, a solid amide-sulfuric acid composition that is to be dissolved to produce an aqueous solution containing 5 weight percent of a combination of amide and sulfuric acid would be diluted by a factor of 19 to 1. Thus, the solid composition should contain approximately 19 times the systemic herbicide component concentration desired in the solution on a weight percent basis. Hence, if a final solution systemic herbicide concentration of 0.1 weight percent is desired, the solid composition should contain approximately 1.9 weight percent of that component.

The amide-sulfuric acid components may contain unreacted (free) sulfuric acid or the di-adduct of sulfuric acid. Useful and preferred proportions of chalcogen compound, sulfuric acid, and of the mono- and di-adducts of sulfuric acid, relative to each other, can be conveniently expressed in terms of the amide/sulfuric acid molar ratio. This ratio will be about ¼ to less than 2, usually within the range of about ¼ to about 7/4, preferably about ½ to about 3/2, and most preferably between about 1/1 and about 3/2. Molar ratios within the range of about ¼ to about 7/4 define compositions in which at least 25 percent of the sulfuric acid is present as the mono-adduct of sulfuric acid. Molar ratios within the range of ½ to about 3/2 define compositions in which at least 50 percent of the sulfuric acid is present as the mono-adduct. The most preferred molar ratio range of about 1/1 to about 3/2 defines compositions which contain essentially no uncomplexed sulfuric acid and in which at least 50 percent of the sulfuric acid is present as the mono-adduct of sulfuric acid. The most preferred combinations have amide/sulfuric acid molar ratios of about 1/1. In such compositions, essentially all of the sulfuric acid is present as the mono-adduct of sulfuric acid, and such compositions are essentially free of uncomplexed sulfuric acid. Substantial amounts of uncomplexed sulfuric acid, i.e. sulfuric acid that is not complexed with an amide as either the mono- or di-adduct, are less preferred, since sulfuric acid, when present in substantial amounts, increases the corrosivity and toxicity of the composition and may chemically denature the systemic herbicide.

The amide-sulfuric acid components can be produced by the reaction of the amide with sulfuric acid by the methods described in my U.S. Pat. No. 4,445,925, the disclosure of which is incorporated herein by reference in its entirety. That patent describes, in part, the manufacture of urea-sulfuric acid components which are free of decomposition products of urea, sulfuric acid, and the mono- or di-urea sulfuric acid adduct, and are particularly preferred for producing the amide-sulfuric acid components of this invention. As described in U.S. Pat. No. 4,445,925, the reaction of urea and sulfuric acid is extremely exothermic and, if not adequately controlled, can result in the decomposition of reactants or products and the formation of decomposition products such as sulfamic acid, ammonium sulfamate, ammonium sulfate, and other materials. Reactions of sulfuric acid with other amides useful in this invention are also exothermic, and similar precautions should be observed, particularly in the manufacture of more concentrated solutions, melts and solids.

Solid amide-sulfuric acid components can be obtained by crystallization from their respective aqueous solutions, as described for urea-sulfuric acid components in my copending application Ser. No. 444,667 (now abandoned), "Methods for Controlling Vegetation," filed Nov. 26, 1982, and my copending application Ser. No. 673,508 filed Nov. 20, 1984 for "Thermally Stable Urea-Sulfuric Acid Compositions and Methods of Manufacture," the disclosures of which are incorporated herein by reference in their entireties. Surfactants, when present, will either crystallize (as described in Ser. No. 444,667) at approximately the same temperature as the amide-sulfuric acid component, or will be entrained with the crystallized sulfuric acid adduct. In the alternative, the surfactant can be added, when desired, to the dry or damp, crystallized amide-sulfuric acid component by any suitable mixing technique.

As described in my copending application Serial No. 444,667, the urea-sulfuric acid aqueous solution there referred to as 18-0-0-17 has a crystallization temperature of 50° F. Designations such as 18-0-0-17 are conventionally used in the agricultural industry to define the weight percentages of nitrogen, phosphorus, potassium and a fourth component, in this case sulfur, contained in a composition. Thus, 18-0-0-18 contains 18 weight percent nitrogen as urea, 0 percent phosphorus, 0 percent potassium, and 17 weight percent sulfur. The 18-0-0-17 solution has a urea/sulfuric acid molar ratio of about 1.2 and contains about 90 weight percent of a combination of urea and sulfuric acid. Urea and sulfuric acid, in combination, constitute 80 weight percent of the aqueous solution designated as 10-0-0-19 in copending application Ser. No. 444,667, which composition has a urea/sulfuric acid molar ratio of about 0.6 and which crystallizes at about 42° F. The aqueous solution designated as 9-0-0-25 comprises approximately 96 weight percent of a combination of urea and sulfuric acid, has a urea/sulfuric acid molar ratio of about 0.4, and crystallizes at 14° F. The indicated crystallization temperatures of the three urea-sulfuric acid aqueous solutions referred to immediately above, and the crystallization temperatures for other formulations of urea and sulfuric acid useful in the composition and methods of this invention, are illustrated, in part, by the isotherms in the ternary phase diagram for urea, sulfuric acid and water in the drawing accompanying copending application Ser. No. 444,667. The crystallization temperatures for other urea-sulfuric acid combinations and for combinations of sulfuric acid and other amides useful in this invention can be determined from that drawing or by cooling the selected solution until crystallization occurs. The crystallized material can be separated from the supernatant aqueous phase by any suitable solid-liquid separation technique such as filtration, centrifugation, decanting, and the like, and the recovered damp solid can be dried by evaporation if desired.

Since lower crystallization temperatures are required to separate the desired amide-sulfuric acid component from the more dilute solutions, it is preferable to begin with more concentrated solutions having higher crystallization points such as the 18-0-0-17 urea-sulfuric acid compositions which contain only about 10 percent water. More concentrated solutions, and those having higher crystallization temperatures, e.g. 77° F., are even more preferred since less cooling is required to obtain a similar quantity of the chalcogen compound-sulfuric acid component.

Substantially anhydrous solid compositions can be obtained by washing the dried, crystallized amide-sulfuric acid component with a strongly hydrophilic solvent such as absolute ethanol or acetone. Ten to 100 weight parts solvent per weight part solute are usually adequate for this purpose. The procedures for making substantially anhydrous urea-sulfuric acid components which contain about one weight percent water or less and are more thermally stable than more hydrous compositions are discussed in my copending application Ser. No. 673,508 referred to above. Such procedures can be employed to make other thermally stable, anhydrous amide-sulfuric acid components useful herein.

The anhydrous mono-adduct-containing components are stable at ambient conditions and have negligible vapor pressure up to their decomposition temperatures, e.g. up to 300° F. for the urea adducts. However, some of these decompose explosively at much lower temperatures in the presence of water. For instance, the hydrous urea-sulfuric acid compositions decompose at 176° F.

The most preferred solid urea composition consisting of the 1/1 urea/sulfuric acid molar adduct has a melting point of about 100° F., and the melting point of the urea-sulfuric acid component increases as the urea/acid ratio deviates from 1:1 in either direction in a manner paralleling the isotherms illustrated in the drawing of Ser. No. 444,667.

The solid and liquid compositions can also be prepared by gradually adding the amide or amides to either dilute or concentrated sulfuric acid with provision for sufficient cooling to maintain the reaction temperature below the thermal decomposition temperature for the given combination of reactants. Thus, for example, urea can be reacted with chilled, 98 percent concentrated sulfuric acid maintained in an ice bath to produce essentially pure urea-sulfuric acid adducts provided that the rate of urea addition is sufficiently slow to prevent overheating.

The monoamide-sulfuric acid adduct accentuates the activity of the systemic component. Little or no improvement in systemic herbicide activity is observed when systemic herbicides are blended with formulations that contain the diamide-sulfuric acid complex and no significant amount of the monoamide-sulfuric acid complex. Accordingly, the most preferred compositions are those in which essentially all of the amide and sulfuric acid are present as the monoamide-sulfuric acid adduct. Compositions containing substantial amounts of the other components can be used although they are not as active as the preferred compositions.

Unreacted, free sulfuric acid is undesirable in most cases since it is not as effective a contact herbicide as the monoamide adduct on an equivalent acid basis, it has little or no beneficial effect on systemic activity, it is more corrosive than is sulfuric acid combined with the amide, and it tends to react with some of the systemic herbicides. Thus, in both the solid and aqueous compositions, at least about 75, usually at least about 85, and preferably at least about 90 percent of the sulfuric acid is present as the mono- and/or diamide-sulfuric acid adduct. Particularly preferred compositions are those that contain essentially no free sulfuric acid; thus, essentially 100 percent of the sulfuric acid would be combined with the amide as the mono- and/or di-adduct. Furthermore, since the monoamide adduct is the most active combined form, at least about 25, usually at least about 50, preferably at least about 70, and most preferably about 80 to about 100 percent of the sulfuric acid is present as the monoamide-sulfuric acid adduct.

The monoamide-sulfuric acid adduct is an active contact herbicide, even in very dilute aqueous solutions and can be used to control a variety of vegetation even in the absence of other herbicides. In addition to its herbicidal activity, the mono-adduct has the advantage that it accentuates the activity of systemic herbicides. For instance, a composition which contains about 85 weight percent urea and sulfuric acid on a combined weight basis, as produced, can be diluted by as much as 200 to 1 with water to produce herbicidally active solutions containing less than 0.5 weight percent solute. Even higher dilution ratios can be employed but are not preferred due to the difficulty involved in applying a sufficient amount of the active monoamide adduct to crop foliage with extremely dilute solutions.

Although the monoamide adducts appear to dissociate to the amide and sulfuric acid in solutions containing significantly less than about 0.5 weight percent combined amide and sulfuric acid, the dissociated components recombine to form the active adduct on the foliage of treated vegetation. This is apparently due to water evaporation and consequent concentration of the amide and sulfuric acid.

While very low monoamide adduct concentrations, e.g. 0.2 percent, or less, generally do not allow for sufficient dosage rates to provide adequate contact herbicidal activity in many instances, they still significantly accentuate the activity of the systemic component. Higher monoamide adduct concentrations are usually employed when the applicator prefers to obtain significant vegetation control as a result of the contact herbicidal activity. Thus, the applied solutions will usually contain at least about 0.5, generally at least about 1, and preferably at least about 5 weight percent amide and sulfuric acid based on the combined weight of those two components.

The concentrated solutions, e.g. those having amide-sulfuric acid concentrations of 85 percent or higher, are very active contact herbicides. However, they are difficult to apply evenly over the foliage due to the relatively low dosage rates required and to their relatively high viscosity.

With these factors in mind, the applied solution will usually contain about 0.5 to about 90, normally about 1 to about 50, and preferably about 5 to about 30 weight percent of the amide and sulfuric acid on a combined weight basis.

It is preferable to manufacture solutions containing relatively high concentrations of the amide and sulfuric acid in order to avoid handling and transporting significant amounts of water. Thus, the compositions, as produced, usually contain at least about 50 and preferably at least about 70 weight percent amide and sulfuric acid on a combined weight basis.

The compositions of this invention may also contain one or more chemically stable surfactants. Surfactants increase the herbicidal activity of both the systemic herbicide component and the amide-sulfuric acid component toward susceptible vegetation and broaden the spectrum of plant species affected by the herbicidal compositions of this invention. Surfactants increase the wetting ability of the liquid compositions for plant foliage, particularly for the foliage of plants that are coated with a significant amount of waxy cuticle, and they facilitate the application of those compositions to foliage and to the soil by spraying or by other means. Many surfactants, particularly nonionic surfactants, are nonreactive and are sufficiently stable to afford significant shelf life. Stability of the surfactant can be measured by the NMR technique described above. Illustrative of classes of stable surfactants are nonionics such as the alkylphenol polyethylene oxides, anionics such as the long chain alkyl sulfates, and cationics such as 1-hydroxyethyl-2-heptadecenyl gloxalidin. Of these, the polyethylene oxide nonionic surfactants are particularly preferred. Illustrative of preferred specific surfactants is the nonionic surfactant marketed by Thompson-Hayward, Inc., under the trademark T-MULZ 891.

Surfactant concentration should be sufficient to increase the foliage wetting ability of the aqueous solution. Increased wetting ability markedly increases both the degree and spectrum of contact herbicidal activity of the monoamide sulfuric acid adduct and improves the herbicidal activity of the systemic component.

Surfactant concentration will usually be at least about 0.05, generally at least about 0.1, and preferably at least about 0.2 weight percent of the aqueous solution as applied. Surfactant concentrations of about 0.2 to about 1 weight percent are adequate in most applications. The concentration of surfactant in the solid compositions of this invention should be sufficient to produce the desired concentration in the aqueous solution to be produced by dissolving the solid in water, and thus can be determined by the procedure used to determine the concentration of the systemic herbicide component in the solid compositions as discussed above.

The solid and liquid compositions can also contain any one or more of the known major and minor plant nutrients and/or soil adjuvants such as phosphorus (from phosphoric acid), magnesium, manganese, potassium, zinc, boron, etc., from the respective oxides, hydroxides, sulfates, nitrates, and the like. They may also contain nitrogen and/or sulfur in addition to that present in the amide and sulfuric acid. Illustrative of other forms of nitrogen and sulfur that can be used are the nitrates such as magnesium nitrate, ammonium compounds such as ammonium phosphate, sulfates such as potassium and ammonium sulfate, and the like. The concentration of these additional major and minor nutrients in the liquid and solid compositions should be sufficient to introduce the desired amount of the selected nutrients to the soil.

Taking all of the foregoing factors into account, the liquid herbicidal compositions comprise about 0.5 to about 90, generally about 1 to about 50, and preferably about 5 to about 30 weight percent of the combination of amide and sulfuric acid [on a dry-weight basis]; at least a herbicidally effective amount of the systemic herbicide component; and, optionally, at least about 0.5, generally at least about 0.1, and preferably at least about 0.2 weight percent of a surfactant stable in the composition. The lower concentrations of the amide-sulfuric acid component are preferred for application to vegetation and/or to the soil, and the higher concentrations are preferred for manufacture, transport and storage. Higher concentrations of the surfactant and systemic herbicide components are preferred in the concentrated solutions of the amide-sulfuric acid component to assure the presence of effective concentrations of all components upon dilution with water prior to application.

The solid compositions of this invention usually contain at least about 50, and preferably at least about 80 weight percent of the amide-sulfuric acid component. The solids will usually contain at least about 20, generally at least about 50, preferably at least about 80 weight percent of the preferred monoamide-sulfuric acid adduct. They also usually contain sufficient amounts of the optional surfactant and systemic herbicide components to assure the presence of an effective concentration of those two components in aqueous solutions produced by dissolving the solid compositions in water prior to or during contacting with the vegetation or soil. Thus, the solid compositions will contain at least about 0.1, usually at least about 0.2, and preferably at least about 0.5 weight percent of the systemic herbicide component sufficient to assure the presence of an effective amount of that component in aqueous solutions produced by dissolving the solid in water. The solid compositions may contain an amount of the optional surfactant component sufficient to provide an effective surfactant concentration in aqueous solutions produced from the solid compositions of this invention. The concentration of surfactant, when used, will correspond to at least about 0.05, usually at least about 0.1, and preferably at least about 0.2 weight percent of the total solid composition.

The liquid herbicidal compositions can be produced by any method capable of producing a solution or dispersion of the systemic herbicide component (and the surfactant and other additives when employed) in an aqueous solution of the amide-sulfuric acid component. Thus, the systemic herbicide can be added to the concentrated amide-sulfuric acid solution during or immediately after its manufacture, or it can be added to the diluted amide-sulfuric acid solution prior to application of the herbicidal composition to the plants and/or soil to be treated. Alternatively, the systemic herbicide can be mixed with the amount of water required to produce a concentrated or dilute aqueous solution, as desired, before or along with the solid or concentrated aqueous amide-sulfuric acid component. Of course, dissolution of the solid compositions of this invention that contain both the amide-sulfuric acid component and the systemic herbicide component, in water, will also result in formation of the herbicidally active liquid compositions of this invention.

In the method of this invention, the novel liquid or solid herbicidal compositions are contacted with the foliage of plants to be controlled (when post emergent control is desired) and/or with the soil (when preemergent control is desired) by spraying, dusting, or otherwise distributing the liquid or solid composition onto the foliage and/or the soil surface. Alternatively, when preemergent control is the principal or sole objective, the liquid or solid compositions can be applied beneath the soil surface by injection or by application to the soil surface during or immediately before plowing, tilling, or other methods of soil mixing.

When the solid compositions are applied to the foliage or to the soil (either topically or subsurface), steps should be taken to assure mixing of the solid composition with water either immediately upon or shortly after its application. This can be readily achieved by any one of several procedures including prewetting the foliage and/or soil with water, wetting the foliage and/or the soil shortly after application of the solid herbicidal compositions, and the like. When the solid is applied to relatively dry foliage or soil, it is preferably wet with sufficient water to assure formation of an aqueous solution of the systemic herbicide and amide-sulfuric acid components on the foliage or in or on the soil within 24 hours, preferably within 10 hours, and most preferably within 1 hour following application of the solid.

In the presently preferred method, the novel liquid compositions are applied directly to the foliage, or to the soil surface or subsurface, rather than being formed in situ from the applied solid as discussed above. The aqueous solutions may be preformed and applied to the foliage, soil, etc., as such, or they can be formed in situ by sequential or simultaneous application of two or more solutions which, when combined, form the novel compositions of this invention. Thus, for example, an amide-sulfuric acid solution and a systemic herbicide-containing solution can be sequentially applied to the foliage or soil to be treated at respective dosage rates correlated to provide a combination that forms the desired solution in situ. It is essential only that the vegetation to be treated be contacted with the described compositions of this invention. Similarly, the surfactant, when employed, can be applied in a separate solution and mixed in situ, with the urea-sulfuric acid and systemic herbicide components. Nevertheless, for convenience and ease of application and control, the use of preformed solutions containing all of the desired components is presently preferred.

The compositions of this invention can also be employed to eliminate undesired vegetation from fields seeded with desired crop plants prior to crop emergence, provided, of course, that the selected systemic herbicide component does not exhibit preemergent activity toward the seeded crop either prior to or after germination. The contact herbicidal activity of the amide-sulfuric acid component dissipates rapidly upon exposure to the soil environment, i.e. within about 24 hours or less. Thus, seeded crops are not damaged when the amide-sulfuric acid component is topically applied, even after germination, particularly when the herbicidal composition is applied at least 24 hours prior to emergence.

The compositions are usually applied at dosage rates corresponding to at least about 50, generally about 50 to about 1000, and preferably about 100 to about 500 pounds per acre of the monoamide-sulfuric acid adduct. These dosage rates correspond to at least about 50, generally about 50 to about 4,000, and preferably about 100 to about 2,000 pounds per acre of the combination of amide and sulfuric acid when using compositions in which at least about 25 percent of the sulfuric acid is present as the monoamide-sulfuric acid adduct.

Relatively higher dosage rates of compositions deviating significantly from the 1/1 amide/sulfuric acid molar ratio composition are required to obtain the same degree of contact herbicidal effectiveness under otherwise identical conditions, i.e. at similar dosage rates with similar plant types. The most significant consideration in this respect is the amount of the monoamide-sulfuric acid adduct applied and retained on the plant foliage or on or in the soil in contact with plant seeds. Thus, higher dosage rates should be used when applying compositions in which only a portion of the sulfuric acid is present as the monoamide adduct, i.e. when a significant amount of the acid is present either as the diurea-sulfuric acid adduct or as free sulfuric acid. Although free sulfuric acid has some herbicidal activity, it is much less active than the monoamide sulfuric acid adducts on an equivalent sulfuric acid basis.

The dosage rate of the systemic herbicide component should be sufficient to accomplish the desired control of treated vegetation and/or plant seeds and can be less than that recommended by the manufacturer of the systemic herbicide component due to the synergistic effect of the amide-sulfuric acid component. Thus, effective dosage rates of the systemic herbicide will be less than about 50, usually about 10 to about 50, and preferably about 10 to about 25 percent of that recommended by the manufacturer. Of course, higher dosage rates of the systemic herbicide can be employed but are not generally required. The absolute dosage rates of the systemic herbicide component will vary widely from one systemic herbicide to the next due to the large differences in specific herbicidal activity between different systemic herbicides. Specific herbicidal activity, as that term is used herein, refers to the absolute amount of a specific herbicide required to accomplish a given degree of vegetation control. The magnitude of the difference in specific herbicidal activity that can exist between different systemic herbicides is illustrated by the fact that Roundup is effective at dosage rates of several ounces per acre while 2,4-dinitrophenol must be applied at rates on the order of 100 pounds per acre or more in order to achieve adequate control.

The dosage rates of the amide-sulfuric acid component and of the systemic herbicide component required to accomplish the desired pre- and/or post-emergent control will generally be within the ranges discussed above for these two components. However, the dosage rate of each component best suited to accomplish the desired degree and duration of control, and the desired degree of selectivity (when selectivity is required), also can be determined by actual greenhouse or field testing. Such tests may involve a series of compositions having different concentrations of each active component and/or a series of tests in which the same composition is applied to different plots of the same plant population in a series of different dosage rates. The dosage rate required to eliminate the selected plants due to the contact herbicidal activity of the amide-sulfuric acid component alone can be readily determined by applying a composition containing only that component to samples of the foliage to be treated, e.g. to separate small areas within the selected field at different dosage rates and observing the extent of plant kill. When effective concentrations and dosage rates are employed, significant necrosis and plant wilting are evident within 10 minutes and will provide an adequate indication of effectiveness. The full extent of plant kill will not be apparent for approximately 2 to 24 hours. In most situations, prescreening tests of that duration are not inordinant. Plant necrosis is clearly indicated within 24 hours by the disappearance, darkening and/or desiccation of plant tissue. The speed and degree of vegetation control increases as dosage rate is increased. Dosage rate is the primary variable so long as the applied volume is not so high that significant runoff occurs from plant foliage.

In the alternative, the initial testing can be done, as described above, using combinations of the amide-sulfuric acid component and the selected systemic herbicide of different concentrations and/or at different dosage rates to determine the optimum composition and dosage rate to control the vegetation in question.

The applicator should observe that a broader spectrum of plant species is affected by the systemic component in the compositions of this invention due to the synergistic effect of the monoamide adduct. That factor should be kept in mind when designing and testing compositions containing selective systemic herbicides for the selective elimination of undesired vegetation in the presence of desired crops. The full extent of weed control and/or crop damage due to the systemic herbicide component will become apparent within the period defined by the manufacturer of the systemic herbicide and will vary from one herbicide to the next. For instance, the full effect of glyphosate isopropylamine salt, a broad spectrum herbicide, is not apparent for approximately 6 to 7 days. In contrast, the degree of control obtained with 2,4-D is generally apparent within 48 hours or less.

The best combination of variables, i.e. systemic herbicide type and concentration, dosage rate, solution concentration amide/sulfuric acid molar ratio, etc., for the entire field can be determined by the test procedures described above, or by other tests that enable the applicator to define effective or optimum ranges for those variables.

The compositions that contain one or more surfactants, the amide-sulfuric acid component, and one or more broad spectrum systemic herbicides, can be used to eliminate essentially all vegetation from the treated area. Even minor amounts of surfactant dramatically increase the contact herbicidal activity of the amide-sulfuric acid component and the spectrum of plant varieties it controls. The activity of that component increases as surfactant concentration is increased within the ranges discussed above to the point that the compositions that contain a significant amount of surfactant, e.g. 0.1 weight percent surfactant as applied, are essentially nonselective. Thus, the surfactant-containing compositions of this invention can be used to control the more resistant plant varieties, such as, volunteer wheat and Russian thistle, even in the absence of a systemic component that is effective for the control of such plant species.

Compositions that do not contain any significant amount of surfactant, e.g. less than 0.05 weight percent surfactant as applied, can be used to selectively control susceptible plants in the presence of more resistant desirable plants, such as crop plants. The tolerance of vegetation to the surfactant-free compositions varies significantly between species. Thus, for example, relatively low dosage rates are required to eliminate morning glory, while higher dosage rates and surfactants are required to kill more xerophytic plants such as onions and garlic, the foliage of which is protected by a significant amount of waxy coating or cuticle.

The foliage and stems of essentially all plants are protected, to some extent, by a waxy cuticle coating, and the degree of such protection can vary significantly from one species to the next. The contact activity of the amide-sulfuric acid component toward different plant species appears to correlate with the degree of protection afforded by the waxy cuticle on a given plant species. Thus, the effect of surfactant on contact activity may be associated with the surfactant's ability to transport the active monoamide adduct and the systemic herbicide components through the protective coating to the plant cell tissue.

Illustrative of crops that are sufficiently tolerant to the surfactant-free compositions of this invention that do not contain a systemic component designed to control such crops are onions (green and dry bulb), leeks, shallots, spring onions, garlic, chives, cotton, broccoli, cauliflower, cabbage (red and green), Brussel sprouts, Chinese cabbage, bok choy, turf, and some cereal crops such as wheat and barley. Thus, weeds can be controlled in the presence of these and other tolerant crops and plants with compositions of this invention containing systemic herbicides that are not toxic to such crops.

The herbicidal compositions and methods of this invention have numerous advantages over compositions and methods available to the art. They dramatically accentuate the activity of both post- and preemergent systemic herbicides and broaden the spectrum of plant varieties that are controlled by the systemic herbicide component. Thus, they reduce the amount of the systemic herbicide component required to achieve a given degree of vegetation control, or, conversely, increase the control achieved with a specific dosage rate of the systemic herbicide component. By reducing the amount of the systemic herbicide required to obtain the desired control of vegetation, the compositions and methods of this invention reduce both the immediate and persistent toxicity of the herbicidal compositions to humans, wild life, and to the environment, and they reduce the residual toxicity remaining on food crops grown in areas treated with the herbicidal compositions of this invention. By reducing the amount of the systemic herbicide component required to obtain the desired degree of vegetation control, the compositions and methods of this invention reduce the cost required for such control.

The useful compositions exhibit significant contact herbicidal activity (in addition to their systemic activity) due to the contact herbicidal activity of the monoamide-sulfuric acid adduct. They afford the applicator and grower with a greater degree of flexibility than is available with other herbicidal compositions and methods of vegetation control since they can be used to selectively eliminate undesired vegetation existing in the presence of more resistant, desired vegetation such as agricultural crops. In the alternative, by appropriate selection of dosage rates of the systemic herbicide component, the compositions can be employed as broad spectrum, general purpose herbicides to control essentially all forms of vegetation in the treated area. The effectiveness of the described herbicidal compositions and methods, and the spectrum of plant varieties they control, can be increased even further by the use of surfactants. Surfactants increase both the contact and systemic herbicidal activity, and increase the number of plant varieties controlled by the novel compositions and methods.

The described compositions have the further advantage of being usable as either solids or liquids, and each can be employed in either concentrated or dilute form, thereby allowing the applicator even further flexibility in selecting methods of application and treatment. The novel compositions and methods allow for the use of complex organic, systemic herbicide components in the presence of relatively concentrated sulfuric acid due to the fact that the amide-sulfuric acid component of these compositions attenuates the destructive activity of concentrated sulfuric acid toward such complex organic molecules. These compositions and methods have the further advantage that they result in the addition of significant amounts of nutrient nitrogen and sulfur to the soil due to the relatively rapid conversion of the amide-sulfuric acid component to nutrient nitrogen and sulfur upon contact with the soil environment. They also result in the addition of acid to the soil which constitutes a significant advantage, particularly in calcareous soils in which the neutralization of basic soil components is desired.

The invention is further described by the following examples which are illustrative of specific modes of practicing the invention and are not intended as limiting the scope of the invention defined by the appended claims.

EXAMPLE 1

Four replicate test plots of six acres each of an established weed population on a cherry orchard floor comprising sowthistle, chickweed, and water grass were foliarly treated with 50 gallons per acre of undiluted 17-0-0-17 containing 0.1 pound per gallon of Solicam ® (also known as Norflurazon) containing the active ingredient 4-chloro-5-(methylamino)-2-(a,a,a-trifluoro-m-tolyl)-3(2H)-pyridazinone. This treatment corresponded to a Solicam ® dosage rate of 5 pounds per acre and resulted in the almost immediate kill of all weed species and 18 weeks of systemic control as indicated by the absence of weed reemergence.

EXAMPLE 2

Four replicate six-acre plots of the weed population described in Example 1 were treated with 8 pounds per acre of Solicam ® (0.27 pound per gallon) in 30 gallons per acre of water. This treatment resulted in no initial kill. Systemic control became apparent after one week and continued through the sixth week after application at which time the weeds reemerged.

EXAMPLE 3

Two replicate ten-acre plots of an established population of henbit, chickweed, and several annual grasses on the floor of an almond orchard were treated by foliar application of 30 gallons per acre of undiluted 17-0-0-17 containing 0.133 pound per gallon (4 pounds per acre) Surflan ®, known by the common name Oryzalin, containing the active ingredient 3,5-dinitro-$N^4$-dipropylsulfanilamide. This treatment resulted in rapid initial kill as evidenced by complete weed population control within 24 hours and 68 days of systemic control.

EXAMPLE 4

Two replicate ten-acre plots of the weed population described in Example 3 were treated with six pounds per acre (0.2 pound per gallon) Surflan ® applied in 30 gallons of water per acre. This treatment resulted in systemic control after three days and effective control for 40 days after which the weed population reemerged.

EXAMPLE 5

Two replicate six-acre plots of an established weed population comprising henbit, chickweed, groundsel, and foxtail on a grape vineyard floor were treated by foliar application of 25 gallons per acre of undiluted 17-0-0-17 containing 0.08 pound per gallon (2 pounds per acre) of Karmex ®, also known as Diuron, containing the active ingredient 3-(3,4-dichlorophenyl)-1,1-dimethylurea. This treatment resulted in rapid initial kill evidenced by complete control of the weed population within 24 hours followed by 60 days of systemic control prior to weed reemergence.

EXAMPLE 6

The operation of Example 5 was repeated by foliar application of the described 17-0-0-17 Karmex ® solution diluted with an equal volume of water to provide 60 gallons per acre spray volume. This treatment resulted in initial weed control within 24 hours and 60 days of systemic control.

EXAMPLE 7

Two replicate six-acre plots of the weed population described in Example 5 were treated by foliar application of four pounds per acre (0.133 pound per gallon) Karmex ® in 30 gallons per acre water. This treatment resulted in apparent systemic control after 24 hours which continued for 42 days prior to weed reemergence.

EXAMPLE 8

Six replicate one-acre plots of an established weed population comprising sowthistle, dandelion, malow, and western henbit on an apple orchard floor were treated by foliar application of 25 gallons per acre 17-0-0-17 containing 0.4 ounce per gallon of Paraquat ® (10 ounces per acre) diluted with an equal volume of water. This treatment resulted in rapid initial kill evidenced by complete weed control within 24 hours and 50 days of continued systemic control prior to weed reemergence.

EXAMPLE 9

Six replicate one-acre plots of the weed population described in Example 8 were treated by foliar application of 32 ounces per acre Paraquat ® diluted with 50 gallons of water per acre (0.64 ounce per gallon). This treatment resulted in immediate systemic control of all weeds except malow and continued systemic control of all weeds except malow for 40 days.

EXAMPLE 10

Six replicate one-acre plots of an established weed population comprising cheese weed, burrclover, sowthistle, henbit and malow on an apple orchard floor were foliarly treated with 25 gallons per acre of 17-0-0-17 diluted with an equal volume of water and containing 0.5 ounce per gallon of Roundup ® (24 ounces per acre dosage rate). This treatment resulted in immediate weed control within 24 hours and 62 days continued systemic control prior to weed reemergence.

EXAMPLE 11

Six replicate one-acre plots of the weed population described in Example 10 were treated by foliar application of 64 ounces per acre of Roundup ® diluted with water to produce 50 gallons per acre spray volume (1.28 ounces Roundup ® per gallon of spray). This treatment resulted in initial systemic kill and 55 days of continued systemic control before weed reemergence.

EXAMPLE 12

Two replicate twenty-acre plots of an established weed population comprising chickweed, groundsel, fiddleneck, nettle, and foxtail in dormant alfalfa were treated by foliar application of 20 gallons per acre undiluted 17-0-0-17 containing 0.025 pound per gallon (0.5 pound per acre) Velpar ®, also known as Hexazinone, containing the active ingredient 3-cyclohexyl-6-(dimethylamino)-1-methyl-1,3,5-triazine-2,4-(1H,3)-dione.
The total herbicide dosage was purposely kept low to avoid damage to the dormant alfalfa crop. This treatment resulted in 95 percent control of all weed species and no detectable damage to the alfalfa crop either before or after its reemergence. The extent of continued systemic control could not be determined due to reemergence of the alfalfa crop.

EXAMPLE 13

Two replicate twenty-acre plots of the weed population described in Example 12 were treated by foliar application of 0.75 pound per acre Velpar ® diluted with water to produce 20 gallons per acre spray volume (0.0375 pound Velpar ® per gallon). This treatment resulted in 95 percent control of chickweed and groundsel but less than 10 percent control of fiddleneck, nettle and foxtail.

EXAMPLE 14

Two replicate 20-acre plots of an established weed population comprising sowthistle, chickweed, clover and foxtail in dormant alfalfa were treated by foliar application of 20 gallons per acre of undiluted 17-0-0-17 containing 0.125 pint per gallon of Furloe ® (2 and ½ pints Furloe ® per acre). As in Examples 12 and 13, herbicide dosage rate was purposely kept low to avoid damage to the dormant alfalfa crop. This treatment resulted in 80 percent control of all weed species.

EXAMPLE 15

Two replicate twenty-acre plots of the weed population described in Example 14 were treated with 3 and ½ pints per acre Furloe ® diluted with water to produce 20 gallons per acre spray volume (0.175 pint Furloe ® per gallon). This treatment resulted in 70 percent control of sowthistle, chickweed, and clover, but less than 10 percent control of foxtail.

EXAMPLE 16

An established weed population comprising chickweed, fiddleneck, foxtail, sowthistle and clover can be controlled by foliar application of 30 gallons per acre of undiluted 17-0-0-17 containing 0.15 pint of Furloe ® per gallon (4 and ½ pints of Furloe ® per acre) and 0.2 weight percent of the non-ionic surfactant marketed by Thompson-Hayward, Inc., under the trademark T-MULZ 891.

EXAMPLE 17

A solid herbicidal composition containing a surfactant and systemic herbicide can be prepared from an 18-0-0-17 solution having a crystallization temperature of 50° F. and containing 38.6 weight percent urea, 52.1 weight percent sulfuric acid, and 9.3 weight percent water. The 18-0-0-17 solution is cooled to a temperature of 34° F. to crystallize the solute which is then separated from the bulk of the water phase in a conventional filter press operated at 34° F. The damp solid is sequentially washed five times in five equal volumes of acetone; 2 weight parts of acetone per weight part of the urea-sulfuric acid component are employed in each washing step. The resulting, substantially anhydrous, urea-sulfuric acid component having a composition corresponding to 19.8-0-0-18.7 is blended with Thompson-Hayward's T-MULZ 891-brand surfactant and Hexazinone to produce a final composition containing 0.6 weight percent T-MULZ 891 and 0.19 weight percent Hexazinone.

EXAMPLE 18

The solid composition produced in Example 17 can be employed to control an established weed population of groundsel, fiddleneck, foxtail, chickweed, burrclover and sowthistle. Equal parts of the described solid composition and water are mixed together to produce an aqueous solution having the composition 9.9-0-0-9.35 containing 0.3 weight percent T-MULZ 891-brand surfactant (0.04 pound per gallon) and 0.095 weight percent Hexazinone (0.013 pound per gallon). The solid readily dissolves in water. The resulting solution can be foliarly applied to the established weed population at a dosage rate of 40 gallons per acre to effect both contact herbicide and systemic herbicide control of all weed species.

EXAMPLE 19

The mono-N-allyl thioformamide adduct of sulfuric acid can be prepared by dissolving 10 gram moles of N-allyl thioformamide in diethylether, chilling to 50° F., and then gradually adding 10 gram moles of 98 percent sulfuric acid pre-chilled to 30° F. at a rate sufficiently slow to maintain the mixture in the flask at a temperature below 50° F. 0.2 pound of Solicam ® can be added to the resulting solution, and the mixture can be diluted with water and employed to control a weed population comprising sowthistle, chickweed, and water grass when applied at a rate equivalent to 4 pounds Solicam ® per acre.

EXAMPLE 20

Ten gram moles of 98 weight percent sulfuric acid and 10 gram moles of 1-(4-aminobenzenesulfonyl)-2-thiourea can be reacted by the procedure described in Example 19 to produce the corresponding equimolar adduct dissolved in the ether-water mixture which can then be mixed with 0.5 pound of Surflan ® to produce an active herbicide mixture. The resulting concentrate can be diluted with water and employed to control a weed population comprising sowthistle, chickweed, and water grass when applied at a rate of 4 pounds Surflan ® per acre.

EXAMPLE 21

Ten gram moles of 98 weight percent sulfuric acid and 10 gram moles of 1-benzoylurea can be reacted by the procedure described in Example 19 to form the corresponding equimolar adduct dissolved in the ether-water mixture. 0.5 pound Karmex ® can be added, and the resulting mixture can be diluted with water and employed to control a weed population comprising sowthistle, chickweed and water grass when applied at a rate of 2 pounds Karmex ® per acre.

EXAMPLE 22

Ten gram moles of 98 weight percent sulfuric acid and ten gram moles of 1,3-bis(2-ethoxyphenyl) carbamide can be reacted by the procedure described in Example 19 to form the corresponding equimolar adduct dissolved in the ether-water mixture. The resulting product can be mixed with 1 ounce of Paraquat ®, and the resulting mixture can be diluted with water and employed to control a weed population comprising sowthistle, chickweed and water grass when applied at a rate of 8 ounces of Paraquat ® per acre.

EXAMPLE 23

Ten gram moles of 98 weight percent sulfuric acid and ten gram moles of 1-(2-bromo-3-methylbutanoyl) carbamide can be reacted by the procedure described in Example 19 to produce the corresponding equimolar adduct dissolved in the ether-water mixture. The resulting solution can be mixed with 0.8 ounce of Roundup ®, and the resulting mixture can be diluted with water and employed to control a weed population comprising henbit, chickweed and annual grasses when applied at a rate corresponding to 32 ounces Roundup ® per acre.

EXAMPLE 24

Ten gram moles of 98 weight percent sulfuric acid and ten gram moles of 1-(4-bromophenyl) carbamide can be reacted by the procedure described in Example 19 to form the corresponding equimolar adduct dissolved in the ether-water solution. To the resulting solution can be added 0.05 pound Velpar ® and the resulting mixture can be diluted with water and employed to control the weed population comprising henbit, chickweed and annual grasses, when applied at a rate equivalent to 0.5 pound Velpar ® per acre.

EXAMPLE 25

Ten gram moles of 98 weight percent sulfuric acid and 10 gram moles of 1,3-diacetyl carbamide can be reacted by the procedure described in Example 19 to form the corresponding equimolar adduct dissolved in the ether-water solution. 0.25 pint of Furloe ® can be added to the resulting solution, and the resulting concentrate can be employed directly to control a weed population comprising sowthistle, henbit, chickweed and morning glory when applied at a rate corresponding to 32 ounces Furloe ® per acre.

EXAMPLE 26

Ten gram moles of 98 weight percent sulfuric acid and ten gram moles of 1-ethyl-2-selenourea can be reacted by the procedure described in Example 19 to form the corresponding equimolar adduct dissolved in the ether-water solution 0.2 pound of Surflan ® can be added to the resulting solution, and the concentrate can be diluted with an equal volume of water and employed to control a weed population comprising henbit, chickweed and morning glory when applied at a rate corresponding to 4 pounds Surflan per acre.

EXAMPLE 27

The mono-biuret adduct of sulfuric acid can be prepared by reacting ten gram moles of biuret with ten gram moles of sulfuric acid (98 percent concentrate) by the procedure described in Example 19. The resulting solution can be diluted with an equal volume of water mixed with 0.1 pound Solicam ®, and employed to control a weed population comprising groundsel, fiddleneck, foxtail, chickweed, burrclover, and sowthistle when applied foliarly at a rate corresponding to 4 pounds Solicam ® per acre.

EXAMPLE 28

Ten gram moles of thiourea can be reacted with ten gram moles of sulfuric acid (0.98 weight percent concentrate) by the procedure described in Example 19 to form the mono-thiourea adduct of sulfuric acid. The resulting solution can be diluted with two volumes of water and mixed with 0.1 pound Karmex ®. The resulting solution can be employed to control a weed population comprising foxtail, fiddleneck, chickweed and burrclover when applied at a rate corresponding to 2 pounds Karmex ® per acre.

EXAMPLE 29

The mono-formamide adduct of sulfuric acid can be formed by reacting ten gram moles of formamide with ten gram moles of sulfuric acid (98 weight percent concentrated) by the procedure described in Example 19 to form the corresponding mono-formamide adduct of sulfuric acid. The resulting concentrate can be mixed with 0.8 ounce of Roundup ®, diluted with two volumes of water per volume of concentrate, and employed to control a weed population comprising chickweed, groundsel, fiddleneck and burrclover when applied at a rate corresponding to 32 ounces Roundup ® per acre.

EXAMPLE 30

Ten gram moles of N,N-methylphenyl formamide can be reacted with ten gram moles of sulfuric acid (98 weight percent concentrated) by the procedure described in Example 19 to form the corresponding equimolar, mono-N-N-methylphenyl formamide adduct of sulfuric acid. 0.05 pound Velpar ® can be mixed with the resulting concentrate, and this mixture can be diluted with an equal volume of water and employed to control a weed population comprising fiddleneck, chickweed, foxtail, sowthistle and clover when applied at a rate corresponding to 0.5 pound Velpar ® per acre.

While particular embodiments of the invention have been described, it will be understood, of course, that the invention is not limited thereto since many obvious modifications can be made, and it is intended to include within this invention any such modifications as will fall within the scope of the appended claims.

What is claimed is:

1. A herbicidal composition comprising a herbicidally effective amount of a combination of a systemic herbicide stable in said composition and a monoadduct of sulfuric acid with a compound, other than urea, having the formula:

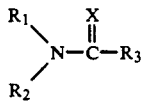

wherein X is selected from the group consisting of oxygen and sulfur; $R_1$ is hydrogen; and each of $R_2$ and $R_3$ is independently selected from the group consisting of hydrogen, $C_3$ to $C_{10}$ substituted or unsubstituted cyclic radicals, $C_1$ to $C_{10}$ substituted or unsubstituted acyclic radicals, $C_3$ to $C_{10}$ substituted or unsubstituted cyclic radicals containing one or more heteroatoms, and $C_1$ to $C_{10}$ substituted or unsubstituted acyclic radicals containing one or more heteroatoms wherein (a) said substituents are selected from the group consisting of thiol, hydroxy, nitro, amino, nitrile, amide, ester, and halogen groups, and (b) said heteroatoms are selected from the group consisting of sulfur, nitrogen, oxygen, and phosphorus atoms.

2. A herbicidal composition comprising a herbicidally effective amount of a combination of a systemic herbicide stable in said composition and a monoadduct of sulfuric acid and one or more members selected from the group consisting of biuret, triuret, formamide, thioformamide, dimethylformamide, thiourea, mono-N-allyl thioformamide, 1-(4-aminobenzenesulfonyl)-2-thiourea, 1-benzoylurea, 1,3-bis(2-ethoxyphenyl) carbamide, 1-(2-bromo-3-methylbutanoyl) carbamide, 1-(4-bromophenyl) carbamide, 1,3-diacetyl carbamide, 1-ethyl-2-selenourea and N,N-methylphenyl formamide.

3. The composition defined in any one of claims 1 or 2, wherein said composition is free of unadducted sulfuric acid.

4. The composition defined in any one of claims 1 or 2 further comprising a surfactant.

5. The composition defined in any one of claims 1 or 2, comprising an amount of said adduct sufficient to accentuate the herbicidal activity of said systemic herbicide.

6. The composition defined in any one of claims 1 or 2, comprising at least about 1 weight percent of said adduct.

7. The composition defined in any one of claims 1 or 2, wherein said systemic herbicide is a postemergent systemic herbicide.

8. The composition defined in any one of claims 1 or 2, wherein said adduct comprises at least about 5 weight percent of said composition, and said systemic herbicide comprises at least about 0.1 weight percent of said composition.

9. The composition defined in any one of claims 1 or 2, wherein at least 50 weight percent of the sulfuric acid present in said composition is present in the form of said monoadduct, the concentration of said monoadduct is sufficient to accentuate the herbicidal activity of said systemic herbicide, and said systemic herbicide comprises a postemergent systemic herbicide.

10. The composition defined in any one of claims 1 or 2, wherein said composition is solid.

11. The composition defined in claim 10, wherein at least 50 percent of the sulfuric acid present in said composition is present in the form of said monoadduct, the concentration of said monoadduct is sufficient to accentuate the herbicidal activity of said systemic herbicide, and said systemic herbicide comprises a postemergent systemic herbicide.

12. A method for controlling vegetation, which comprises applying to said vegetation a herbicidally effective amount of the composition defined in claim 2.

13. A method for controlling vegetation, which comprises applying to said vegetation a herbicidally effective amount of the composition defined in claim 3.

14. A method for controlling vegetation, which comprises applying to said vegetation a herbicidally effective amount of the composition defined in claim 4.

15. A method for controlling vegetation, which comprises applying to said vegetation a herbicidally effective amount of the composition defined in claim 7.

16. A method for controlling vegetation, which comprises applying to said vegetation a herbicidally effective amount of the composition defined in claim 9.

17. A herbicidal composition as defined by claim 2 wherein said monoadduct is a monoadduct of sulfuric acid and one or more members selected from the group consisting of biuret, triuret, formamide, thioformamide, dimethylformamide and thiourea.

18. A method for controlling vegetation which comprises applying to said vegetation a herbicidally effective amount of the composition defined in claim 17.

19. A method for controlling the growth of vegetation which comprises contacting said vegetation with a herbicidally effective amount of a composition comprising a systemic herbicide stable in said composition and a monoadduct of sulfuric acid with a compound, other than urea, having the formula:

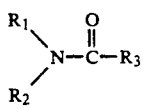

wherein X is selected from the group consisting of oxygen and sulfur; $R_1$ is hydrogen; and each of $R_2$ and $R_3$ is independently selected from the group consisting of hydrogen, $C_3$ to $C_{10}$ substituted or unsubstituted cyclic radicals, $C_1$ to $C_{10}$ substituted or unsubstituted acyclic radicals, $C_3$ to $C_{10}$ substituted or unsubstituted cyclic radicals containing one or more heteroatoms, and $C_1$ to $C_{10}$ substituted or unsubstituted acyclic radicals containing one or more heteroatoms wherein (a) said substituents are selected from the group consisting of thiol, hydroxy, nitro, amino, nitrile, amide, ester, and halogen groups, and (b) said heteroatoms are selected from the group consisting of sulfur, nitrogen, oxygen, and phosphorus atoms.

20. A method as defined by claim 19 wherein said composition further comprises a surfactant.

21. A method as defined by claim 19 wherein said monoadduct and said systemic herbicide comprise, respectively, at least about 5 weight percent and at least about 0.1 weight percent of said composition.

22. A method as defined by claim 19 wherein at least 50 percent of the sulfuric acid present in said composition is present in the form of said monoadduct, the concentration of said monoadduct is sufficient to accentuate the herbicidal activity of said systemic herbicide and said systemic herbicide comprises a postemergent systemic herbicide.

23. A method as defined by claim 19 wherein said vegetation is contacted with said composition at a dosage rate of said systemic herbicide which corresponds to about 50 percent or less of the manufacturer's recommended dosage rate.

24. A method as defined by claim 23 wherein the dosage rate of said systemic herbicide is between 10 and 25 percent of that recommended by the manufacturer.

25. The herbicidal composition of claim 2 further comprising a surfactant.

26. The herbicidal composition of claim 2 wherein said monoadduct and said systemic herbicide comprise, respectively, at least about 5 weight percent and at least about 0.1 weight percent of said composition.

27. The herbicidal composition of claim 2 comprising at least about 1 weight percent of said adduct.

28. The herbicidal composition of claim 2 wherein at least 50 weight percent of the sulfuric acid present in said composition is present in the form of said monoadduct, the concentration of said monoadduct is sufficient to accentuate the herbicidal activity of said systemic herbicide, and said systemic herbicide comprises a postemergent herbicide.

29. A method for controlling vegetation which comprises applying to said vegetation a herbicidally effective amount of the composition defined in claim 25.

* * * * *

UNITED STATES PATENT AND TRADEMARK OFFICE
CERTIFICATE OF CORRECTION

PATENT NO. : 5,288,692

DATED : February 22, 1994

INVENTOR(S) : Donald C. Young

It is certified that error appears in the above-indentified patent and that said Letters Patent is hereby corrected as shown below:

Title page, item [63], column 1, line 2 under "Related U.S. Application Data," after "continuation-in-part of" insert -- Ser. No. 06/771,259, Aug. 30, 1985, Pat. No. 4,722,986, a continuation-in-part of -- .

Title sheet, page 2, column 2, line 8, delete "93,93:990069b" and insert -- 93,93:90069b --.

Column 1, line 7, after "Feb. 19, 1991, which" delete "was" and insert -- is --; line 8, after "continuation-in-part of" delete "my copending application" and insert -- applications Ser. No. 06/771,259, filed Aug. 30, 1985, now U.S. Pat. No. 4,722,986, issued Feb. 2, 1988, --.

Column 23, claim 2, line 65, delete "mono-N-" and insert -- N- --.

Column 25, claim 19, line 8, after "$R_2$ and" delete "$R^3$" and insert -- $R_3$ --.

Signed and Sealed this

Eleventh Day of October, 1994

Attest:

BRUCE LEHMAN

Attesting Officer

Commissioner of Patents and Trademarks